US00PP17611P2

(12) United States Plant Patent
Proud

(10) Patent No.: US PP17,611 P2
(45) Date of Patent: Apr. 17, 2007

(54) ***ELAEOCARPUS* PLANT NAMED 'MONPROUD'**

(50) Latin Name: *Elaeocarpus decipiens*
Varietal Denomination: Monproud

(75) Inventor: Andrew Scott Proud, Glendora, CA (US)

(73) Assignee: Monrovia Growers, Azusa, CA (US)

( * ) Notice: Subject to any disclaimer, the term of this patent is extended or adjusted under 35 U.S.C. 154(b) by 0 days.

(21) Appl. No.: 11/248,675

(22) Filed: Oct. 12, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
(74) *Attorney, Agent, or Firm*—C. A. Whealy

(57) ABSTRACT

A new and distinct cultivar of *Elaeocarpus* plant named 'Monproud', characterized by its upright, columnar and compact plant habit; relatively slow growth rate; short internodes and relatively small leaves; dense and bushy plant form; and elliptically-shaped, undulate and twisting leaves that are initially bronzed green in color becoming dark green with development.

1 Drawing Sheet

Botanical designation: *Elaeocarpus decipiens.*
Cultivar denomination: 'Monproud'.

BACKGROUND OF THE INVENTION

The present Invention relates to a new and distinct cultivar of *Elaeocarpus* plant, botanically known as *Elaeocarpus decipiens,* and hereinafter referred to by the cultivar name Monproud.

The new *Elaeocarpus* originated from a cross-pollination of an unnamed selection of *Elaeocarpus decipiens,* not patented, as the female, or seed, parent with an unnamed selection of *Elaeocarpus decipiens,* not patented, as the male, or pollen, parent. The new *Elaeocarpus* was selected as a single plant from the resulting progeny of the cross-pollination by the Inventor in a controlled environment in Azusa, Calif. in August, 2001.

Asexual reproduction of the new cultivar by terminal cuttings in a controlled environment in Azusa, Calif., since October, 2001, has shown that the unique features of this new *Elaeocarpus* are stable and reproduced true to type in successive generations.

SUMMARY OF THE INVENTION

Plants of the cultivar Monproud have not been observed under all possible environmental conditions. The phenotype may vary somewhat with variations in environment and culture such as temperature and light intensity, without, however, any variance in genotype.

The following traits have been repeatedly observed and are determined to be the unique characteristics of 'Monproud'. These characteristics in combination distinguish 'Monproud' as a new and distinct *Elaeocarpus* cultivar:

1. Upright, columnar and compact plant habit.
2. Relatively slow growth rate.
3. Short internodes and relatively small leaves; dense and bushy plant form.

4. Elliptically-shaped, undulate and twisting leaves that are initially bronzed green in color becoming dark green with development.

Plants of the new *Elaeocarpus* can be compared to plants of the parent selections and other selections of *Elaeocarpus* known to the Inventor. In side-by-side comparisons conducted in Azusa, Calif., plants of the new *Elaeocarpus* differed from plants of the parent selections and other selections of *Elaeocarpus* known to the Inventor in the following characteristics:

1. Plants of the new *Elaeocarpus* had shorter internodes than plants of the parent selections and other selections known to the Inventor.
2. Plants of the new *Elaeocarpus* had smaller leaves than plants of the parent selections and other selections known to the Inventor.
3. Leaves of plants of the new *Elaeocarpus* were more undulate and twisting and had more pronounced venation than leaves of plants of the parent selections and other selections known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Elaeocarpus.*

The photograph at the bottom of sheet comprises a side perspective view of a typical plant of 'Monproud' grown in a container.

The photograph at the top of the sheet comprises a close-up view of typical leaves of 'Monproud'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown in five-gallon containers in an outdoor nursery for about three years in Azusa, Calif. During the production of the plants, day temperatures ranged from about 24° C. to about 29° C. and night temperatures ranged from about 4° C. to about 12° C.

Botanical classification: *Elaeocarpus decipiens* cultivar Monproud.

Parentage:

*Female, or seed, parent.*—Unnamed selection of *Elaeocarpus decipiens,* not patented.

*Male, or pollen, parent.*—Unnamed selection of *Elaeocarpus decipiens,* not patented.

Propagation:

*Type cutting.*—Terminal cuttings.

*Time to produce a rooted young plant.*—About 80 days.

*Root description.*—Thick, woody with age; new roots, reddish white, with development becoming closer to light brown.

*Rooting habit.*—Freely branching.

Plant description:

*Form.*—Perennial shrub; compact, upright and columnar plant habit; relatively slow growth rate. Short internodes and relatively small leaves; dense and bushy plant form. Freely branching; about 26 lateral branches per plant.

*Plant height.*—About 98 cm.

*Plant diameter.*—About 58 cm.

*Lateral branches.*—Length: About 38 cm. Diameter: About 1.2 cm. Internode length: About 1.5 cm. Strength: Strong. Texture: Smooth, glabrous. Color, young: Close to 144A. Color, woody: Close to 201A.

*Foliage description.*—Arrangement: Alternate; simple. Length: About 8.4 cm. Width: About 2.3 cm. Shape: Elliptic. Aspect: Twisting. Apex: Acute. Base: Attenuate. Margin: Shallowly serrate; undulate. Texture, upper and lower surfaces: Smooth, glabrous; tough, leathery. Venation pattern: Pinnate, arcuate. Color: Developing foliage, upper and lower surfaces: Close to 146A overlain with close to 184A. Fully expanded foliage, upper surface: Close to 147A; with development, overlain with close to 42A. Fully expanded foliage, lower surface: Close to 148A. Venation, upper surface: Close to 144A. Venation, lower surface: Midrib, close to 185A; lateral veins, close to 148A. Petiole length: About 1 cm. Petiole diameter: About 2 mm. Petiole texture, upper and lower surfaces: Smooth, glabrous. Petiole color, upper surface: Close to 184A. Petiole color, lower surface: Close to 146D.

Flower description: Flower development has not been observed on plants of the new *Elaeocarpus*.

Disease/pest resistance: Plants of the new *Elaeocarpus* grown in the garden have not been noted to be resistant to pathogens and pests common to *Elaeocarpus*.

Weather tolerance: Plants of the new *Elaeocarpus* have been observed to be very tolerant to rain and wind.

Temperature tolerance: Plants of the new *Elaeocarpus* have been observed to be tolerant to temperatures ranging from −12° C. to 43° C.

It is claimed:

1. A new and distinct cultivar of *Elaeocarpus* plant named 'Monproud', as illustrated and described.

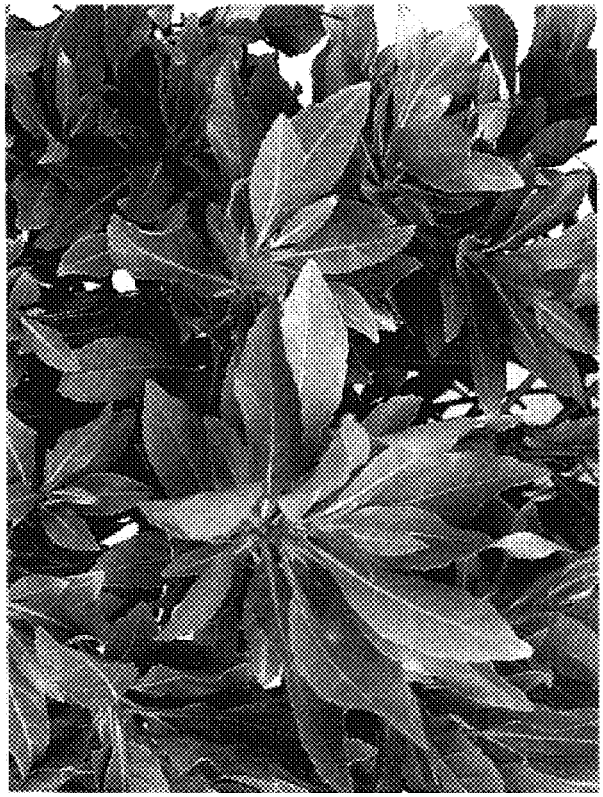
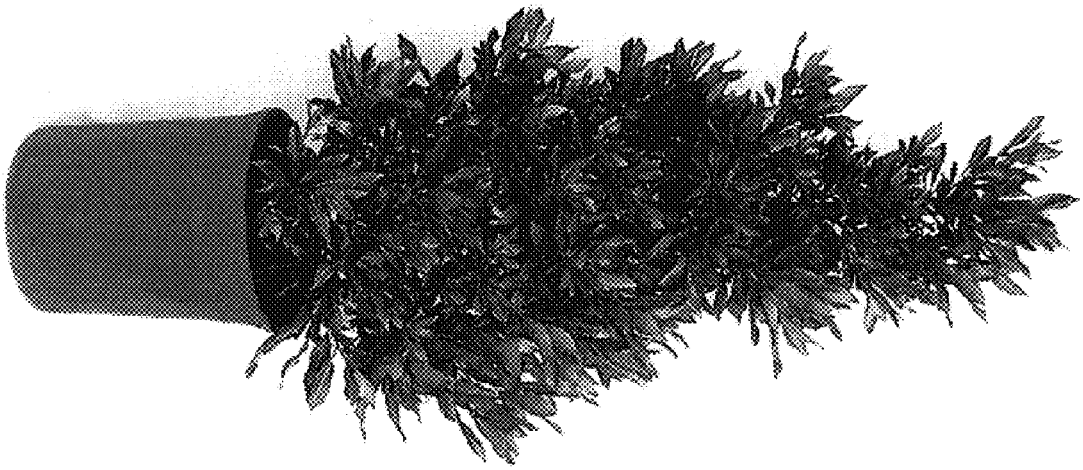

* * * * *